United States Patent
Gilbert et al.

(10) Patent No.: US 8,762,165 B2
(45) Date of Patent: *Jun. 24, 2014

(54) OPTIMIZING TEST PROCEDURES FOR A SUBJECT UNDER TEST

(75) Inventors: Harry M. Gilbert, Portage, MI (US);
Alex Portyanko, Portage, MI (US);
Randy L. Mayes, Otsego, MI (US);
Gregory J. Fountain, Kalamazoo, MI (US); William Wittliff, III, Gobles, MI (US)

(73) Assignee: Bosch Automotive Service Solutions LLC, Warren, MI (US)

( * ) Notice: Subject to any disclaimer, the term of this patent is extended or adjusted under 35 U.S.C. 154(b) by 619 days.

This patent is subject to a terminal disclaimer.

(21) Appl. No.: 12/982,975

(22) Filed: Dec. 31, 2010

(65) Prior Publication Data

US 2011/0161104 A1 Jun. 30, 2011

Related U.S. Application Data

(63) Continuation-in-part of application No. 11/452,249, filed on Jun. 14, 2006, now Pat. No. 7,865,278.

(51) Int. Cl.
*G06F 19/00* (2011.01)
*G06Q 50/00* (2012.01)
*G06Q 50/22* (2012.01)
*G06Q 50/24* (2012.01)

(52) U.S. Cl.
CPC ............... *G06F 19/34* (2013.01); *G06F 19/32* (2013.01); *G06F 19/325* (2013.01); *G06F 19/3418* (2013.01); *G06Q 50/22* (2013.01); *G06Q 50/24* (2013.01)
USPC .................................................. 705/2; 705/3

(58) Field of Classification Search
CPC ......... G06F 19/34; G06Q 50/22; G06Q 50/24
USPC ....................................................... 705/2–3
See application file for complete search history.

(56) References Cited

U.S. PATENT DOCUMENTS

| 4,404,639 A | 9/1983 | McGuire et al. |
| 4,757,463 A | 7/1988 | Ballou et al. |

(Continued)

FOREIGN PATENT DOCUMENTS

| CN | 1527934 A | 9/2004 |
| DE | 10233503 A1 | 2/2004 |

(Continued)

OTHER PUBLICATIONS

B. Ives et al., "After the Sale: Leveraging Maintenance with Information Technology," MIS Quarterly, vol. 12, No. 1, Mar. 1988, pp. 7-21.

(Continued)

*Primary Examiner* — Sheetal R Rangrej
(74) *Attorney, Agent, or Firm* — Baker & Hostetler LLP (57) ABSTRACT

In a computer-implemented method of optimizing a diagnostic test sequence to diagnose a medical condition of a subject. A group of diagnostic tests related to a symptom is determined from a pool of diagnostic tests. A probabilistic failure mode analysis is conducted to determine the efficacy of each of the diagnostic tests based on historical outcomes of actual diagnostic testing. The comparative utility of each diagnostic tests based on a plurality of factors that can affect problem resolution is analyzed. A weight is assigned to each factor involved in the probabilistic failure mode analysis. The diagnostic tests are ordered based upon at least one of: a probability of the diagnostic test identifying a cause of the failure mode in a minimum amount of time; a probability of the diagnostic test identifying the cause of the failure mode at a minimum cost; and a relative weighting of minimizing time versus minimizing cost. A first diagnostic test is selected from the group based at least in part on a probabilistic failure mode analysis and the weighted factors involved therein.

30 Claims, 6 Drawing Sheets

(56) References Cited

U.S. PATENT DOCUMENTS

| | | | |
|---|---|---|---|
| 4,796,206 A | 1/1989 | Boscove et al. | |
| 4,817,092 A | 3/1989 | Denny | |
| 4,866,635 A | 9/1989 | Kahn et al. | |
| 4,873,687 A | 10/1989 | Breu | |
| 4,881,230 A | 11/1989 | Clark et al. | |
| 4,943,919 A | 7/1990 | Aslin et al. | |
| 4,954,964 A | 9/1990 | Singh | |
| 4,964,125 A | 10/1990 | Kim | |
| 4,985,857 A | 1/1991 | Bajpai et al. | |
| 5,010,487 A | 4/1991 | Stonehocker | |
| 5,023,791 A | 6/1991 | Herzberg et al. | |
| 5,025,392 A | 6/1991 | Singh | |
| 5,036,479 A | 7/1991 | Prednis et al. | |
| 5,099,436 A | 3/1992 | McCown et al. | |
| 5,109,380 A | 4/1992 | Ogino | |
| 5,111,402 A | 5/1992 | Brooks et al. | |
| 5,127,005 A | 6/1992 | Oda et al. | |
| 5,161,158 A | 11/1992 | Chakravarty et al. | |
| 5,184,312 A | 2/1993 | Ellis | |
| 5,214,577 A | 5/1993 | Sztipanovits et al. | |
| 5,270,920 A | 12/1993 | Pearse et al. | |
| 5,293,323 A | 3/1994 | Doskocil et al. | |
| 5,396,422 A | 3/1995 | Forchert et al. | |
| 5,442,549 A | 8/1995 | Larson | |
| 5,491,631 A | 2/1996 | Shirane et al. | |
| 5,524,078 A | 6/1996 | Kolb et al. | |
| 5,541,840 A | 7/1996 | Gurne et al. | |
| 5,561,762 A | 10/1996 | Smith et al. | |
| 5,572,424 A | 11/1996 | Kellogg et al. | |
| 5,586,252 A | 12/1996 | Barnard et al. | |
| 5,617,039 A | 4/1997 | Kuck et al. | |
| 5,631,831 A | 5/1997 | Bird et al. | |
| 5,670,939 A | 9/1997 | Rodewald et al. | |
| 5,671,141 A | 9/1997 | Smith et al. | |
| 5,696,676 A | 12/1997 | Takaba | |
| 5,729,452 A | 3/1998 | Smith et al. | |
| 5,742,500 A | 4/1998 | Irvin | |
| 5,778,381 A | 7/1998 | Sandifer | |
| 5,812,984 A * | 9/1998 | Goltra | 705/3 |
| 5,835,871 A | 11/1998 | Smith et al. | |
| 5,838,261 A | 11/1998 | Lauta et al. | |
| 5,852,789 A | 12/1998 | Trsar et al. | |
| 5,883,586 A | 3/1999 | Tran et al. | |
| 5,916,286 A | 6/1999 | Seashore et al. | |
| 5,964,811 A | 10/1999 | Ishii et al. | |
| 5,964,813 A | 10/1999 | Ishii et al. | |
| 5,987,443 A | 11/1999 | Nichols et al. | |
| 6,003,021 A | 12/1999 | Zadik et al. | |
| 6,003,808 A | 12/1999 | Nguyen et al. | |
| 6,006,146 A | 12/1999 | Usui et al. | |
| 6,012,152 A | 1/2000 | Douik et al. | |
| 6,032,088 A | 2/2000 | Feldmann et al. | |
| 6,041,287 A | 3/2000 | Dister et al. | |
| 6,055,468 A | 4/2000 | Kaman et al. | |
| 6,064,998 A | 5/2000 | Zabloudil et al. | |
| 6,067,537 A | 5/2000 | O'Connor et al. | |
| 6,067,538 A | 5/2000 | Zorba et al. | |
| 6,073,127 A | 6/2000 | Lannert et al. | |
| 6,085,184 A | 7/2000 | Bertrand et al. | |
| 6,119,074 A | 9/2000 | Sarangapani | |
| 6,122,575 A | 9/2000 | Schmidt et al. | |
| 6,134,488 A | 10/2000 | Sasaki et al. | |
| 6,141,608 A | 10/2000 | Rother | |
| 6,167,352 A | 12/2000 | Kanevsky et al. | |
| 6,175,787 B1 | 1/2001 | Breed | |
| 6,192,302 B1 | 2/2001 | Giles et al. | |
| 6,205,465 B1 | 3/2001 | Schoening et al. | |
| 6,226,627 B1 | 5/2001 | Polak | |
| 6,236,917 B1 | 5/2001 | Liebl et al. | |
| 6,249,755 B1 | 6/2001 | Yemini et al. | |
| 6,263,268 B1 | 7/2001 | Nathanson | |
| 6,263,322 B1 | 7/2001 | Kirkevold et al. | |
| 6,282,469 B1 | 8/2001 | Rogers et al. | |
| 6,301,531 B1 | 10/2001 | Pierro et al. | |
| 6,314,375 B1 | 11/2001 | Sasaki et al. | |
| 6,330,499 B1 | 12/2001 | Chou et al. | |
| 6,338,148 B1 | 1/2002 | Gillenwater et al. | |
| 6,363,304 B1 | 3/2002 | Ramsey | |
| 6,370,455 B1 | 4/2002 | Larson et al. | |
| 6,383,135 B1 * | 5/2002 | Chikovani et al. | 600/300 |
| 6,434,455 B1 | 8/2002 | Snow et al. | |
| 6,477,453 B1 | 11/2002 | Oi et al. | |
| 6,493,615 B1 | 12/2002 | Johnston | |
| 6,505,106 B1 | 1/2003 | Lawrence et al. | |
| 6,512,968 B1 | 1/2003 | de Bellefeuille et al. | |
| 6,522,987 B1 | 2/2003 | Flink et al. | |
| 6,526,340 B1 | 2/2003 | Reul et al. | |
| 6,526,361 B1 | 2/2003 | Jones et al. | |
| 6,538,472 B1 | 3/2003 | McGee | |
| 6,557,115 B2 | 4/2003 | Gillenwater et al. | |
| 6,560,516 B1 | 5/2003 | Baird et al. | |
| 6,574,537 B2 | 6/2003 | Kipersztok et al. | |
| 6,591,182 B1 | 7/2003 | Cece et al. | |
| 6,609,051 B2 | 8/2003 | Fiechter et al. | |
| 6,611,740 B2 | 8/2003 | Lowrey et al. | |
| 6,615,120 B1 | 9/2003 | Rothner | |
| 6,636,790 B1 | 10/2003 | Lightner et al. | |
| 6,640,166 B2 | 10/2003 | Liebl et al. | |
| 6,643,607 B1 | 11/2003 | Chamberlain et al. | |
| 6,652,169 B2 | 11/2003 | Parry | |
| 6,662,087 B1 | 12/2003 | Liebl et al. | |
| 6,694,235 B2 | 2/2004 | Akiyama | |
| 6,708,092 B1 | 3/2004 | Starks et al. | |
| 6,711,134 B1 | 3/2004 | Wichelman et al. | |
| 6,714,846 B2 | 3/2004 | Trsar et al. | |
| 6,738,697 B2 | 5/2004 | Breed | |
| 6,748,304 B2 | 6/2004 | Felke et al. | |
| 6,751,536 B1 | 6/2004 | Kipersztok et al. | |
| 6,768,935 B1 | 7/2004 | Morgan et al. | |
| 6,795,778 B2 | 9/2004 | Dodge et al. | |
| 6,807,469 B2 | 10/2004 | Funkhouser et al. | |
| 6,819,988 B2 | 11/2004 | Dietz et al. | |
| 6,836,708 B2 | 12/2004 | Tripathi | |
| 6,845,307 B2 | 1/2005 | Rother | |
| 6,845,468 B2 | 1/2005 | James | |
| 6,868,319 B2 | 3/2005 | Kipersztok et al. | |
| 6,874,680 B1 | 4/2005 | Klaus et al. | |
| 6,928,349 B1 | 8/2005 | Namaky et al. | |
| 6,941,203 B2 | 9/2005 | Chen | |
| 6,950,829 B2 | 9/2005 | Schlabach et al. | |
| 6,993,421 B2 | 1/2006 | Pillar et al. | |
| 7,010,460 B2 | 3/2006 | Trsar et al. | |
| 7,013,411 B2 | 3/2006 | Kallela et al. | |
| 7,050,894 B2 | 5/2006 | Halm et al. | |
| 7,062,622 B2 | 6/2006 | Peinado | |
| 7,073,120 B2 | 7/2006 | Torii et al. | |
| 7,082,359 B2 | 7/2006 | Breed | |
| 7,103,610 B2 | 9/2006 | Johnson et al. | |
| 7,103,679 B2 | 9/2006 | Bonn | |
| 7,120,559 B1 | 10/2006 | Williams et al. | |
| 7,120,890 B2 | 10/2006 | Urata et al. | |
| 7,124,058 B2 | 10/2006 | Namaky et al. | |
| 7,142,960 B2 | 11/2006 | Grier et al. | |
| 7,162,741 B2 | 1/2007 | Eskin et al. | |
| 7,165,216 B2 | 1/2007 | Chidlovskii et al. | |
| 7,171,372 B2 | 1/2007 | Daniel et al. | |
| 7,203,881 B1 | 4/2007 | Williams et al. | |
| 7,209,815 B2 | 4/2007 | Grier et al. | |
| 7,209,817 B2 | 4/2007 | Abdel-Malek et al. | |
| 7,209,860 B2 | 4/2007 | Trsar et al. | |
| 7,216,052 B2 | 5/2007 | Fountain et al. | |
| 7,251,535 B2 | 7/2007 | Farchmin et al. | |
| 7,272,475 B2 | 9/2007 | Gawlik et al. | |
| 7,272,756 B2 | 9/2007 | Brink et al. | |
| 7,286,047 B2 | 10/2007 | Oesterling et al. | |
| 7,373,225 B1 | 5/2008 | Grier et al. | |
| 7,376,497 B2 | 5/2008 | Chen | |
| 7,379,846 B1 | 5/2008 | Williams et al. | |
| 7,400,954 B2 | 7/2008 | Sumcad et al. | |
| 7,409,317 B2 | 8/2008 | Cousin et al. | |
| 7,428,663 B2 | 9/2008 | Morton et al. | |
| 7,430,535 B2 | 9/2008 | Dougherty et al. | |
| 7,444,216 B2 | 10/2008 | Rogers et al. | |
| 7,483,774 B2 | 1/2009 | Grichnik et al. | |

(56) References Cited

U.S. PATENT DOCUMENTS

| | | |
|---|---|---|
| 7,555,376 B2 | 6/2009 | Beronja |
| 7,565,333 B2 | 7/2009 | Grichnik et al. |
| 7,610,127 B2 | 10/2009 | D'Silva et al. |
| 7,636,622 B2 | 12/2009 | Underdal et al. |
| 7,643,912 B2 | 1/2010 | Heffington |
| 7,647,349 B2 | 1/2010 | Hubert et al. |
| 7,715,961 B1 | 5/2010 | Kargupta |
| 7,739,007 B2 | 6/2010 | Logsdon |
| 7,751,955 B2 | 7/2010 | Chinnadurai et al. |
| 7,752,224 B2 | 7/2010 | Davis et al. |
| 7,761,591 B2 | 7/2010 | Graham |
| 7,765,040 B2 | 7/2010 | Underdal et al. |
| 7,778,746 B2 | 8/2010 | McLeod et al. |
| 7,788,096 B2 | 8/2010 | Chelba et al. |
| 7,809,482 B2 | 10/2010 | Bertosa et al. |
| 7,853,435 B2 | 12/2010 | Dodge et al. |
| 7,860,620 B2 | 12/2010 | Kojitani et al. |
| 7,865,278 B2 * | 1/2011 | Underdal et al. ............ 701/31.8 |
| 7,882,394 B2 | 2/2011 | Hosek et al. |
| 7,925,397 B2 | 4/2011 | Underdal et al. |
| 8,019,501 B2 | 9/2011 | Breed |
| 8,024,083 B2 | 9/2011 | Chenn |
| 8,055,907 B2 | 11/2011 | Deem et al. |
| 8,239,094 B2 | 8/2012 | Underdal et al. |
| 2002/0007237 A1 | 1/2002 | Phung et al. |
| 2002/0059075 A1 | 5/2002 | Schick et al. |
| 2002/0091736 A1 | 7/2002 | Wall |
| 2002/0112072 A1 | 8/2002 | Jain |
| 2002/0116669 A1 | 8/2002 | Jain |
| 2002/0173885 A1 | 11/2002 | Lowrey et al. |
| 2003/0177414 A1 | 9/2003 | Pillutla et al. |
| 2004/0001106 A1 | 1/2004 | Deutscher et al. |
| 2004/0039493 A1 | 2/2004 | Kaufman |
| 2004/0181688 A1 | 9/2004 | Wittkotter |
| 2005/0043868 A1 | 2/2005 | Mitcham |
| 2005/0065678 A1 | 3/2005 | Smith et al. |
| 2005/0071143 A1 | 3/2005 | Tran et al. |
| 2005/0137762 A1 | 6/2005 | Rother |
| 2005/0144183 A1 | 6/2005 | McQuown et al. |
| 2005/0177352 A1 | 8/2005 | Gravel |
| 2005/0222718 A1 | 10/2005 | Lazarz et al. |
| 2006/0030981 A1 | 2/2006 | Robb et al. |
| 2006/0074824 A1 | 4/2006 | Li |
| 2006/0095230 A1 | 5/2006 | Grier et al. |
| 2006/0129906 A1 | 6/2006 | Wall |
| 2006/0136104 A1 | 6/2006 | Brozovich et al. |
| 2006/0142907 A1 | 6/2006 | Cancilla et al. |
| 2006/0142910 A1 | 6/2006 | Grier et al. |
| 2006/0149434 A1 | 7/2006 | Bertosa et al. |
| 2006/0210141 A1 | 9/2006 | Kojitani et al. |
| 2006/0229777 A1 | 10/2006 | Hudson et al. |
| 2007/0100520 A1 | 5/2007 | Shah et al. |
| 2007/0124282 A1 | 5/2007 | Wittkotter |
| 2007/0226540 A1 | 9/2007 | Konieczny |
| 2007/0250228 A1 | 10/2007 | Reddy et al. |
| 2007/0293998 A1 | 12/2007 | Underdal et al. |
| 2007/0294001 A1 | 12/2007 | Underdal et al. |
| 2009/0216584 A1 | 8/2009 | Fountain et al. |
| 2009/0271066 A1 | 10/2009 | Underdal et al. |
| 2010/0082197 A1 | 4/2010 | Kolbet et al. |
| 2010/0262431 A1 | 10/2010 | Gilbert |
| 2011/0046972 A1 * | 2/2011 | Leverette ........................ 705/2 |

FOREIGN PATENT DOCUMENTS

| | | |
|---|---|---|
| DE | 10332203 A1 | 2/2005 |
| EP | 1674958 A1 | 6/2006 |
| GB | 2329943 A | 4/1999 |
| JP | H03-087671 A | 4/1991 |
| JP | 06265596 | 9/1994 |
| JP | H08-043265 A | 2/1996 |
| JP | H10-253504 A | 9/1998 |
| JP | 2001-202125 A | 7/2001 |
| JP | 2001-229299 A | 8/2001 |
| JP | 2002-183334 A | 6/2002 |
| JP | 2004-299587 A | 10/2004 |
| JP | 2007-326425 A | 12/2007 |

OTHER PUBLICATIONS

"Volkswagon-Audi Vehicle Communication Software Manual," Snap-On, published Mar. 31, 2006, http://www.w124performance.com/docs/general/Snap-On/manuals/VCS_Manual_VW_Audi.pdf, XP007920392.

Tariq Assaf, et al. "Automatic Generation of Diagnostic Expert Systems from Fault Trees," 2003 Proceedings Annual Reliability and Maintainability Symposium, pp. 143-147.

European Search Report for Appl. No. 07252442.4, dated Sep. 11, 2007.

European Search Report for Appl. No. 07252441, dated Jun. 20, 2008.

L.J. Aartman, et al., "An Independent Verification Tool for Multi-Vendor Mode S Airborne Transponder Conformance Testing," 21st Digital Avionics Systems Conference, 2002, pp. 12.E.5-1-12.E.5-11, vol. 2.

"Annex A Test Bit Sequence," Methodology for Jitter and Signal Quality; Specification-MJSQ Technical Report REV 10.0, pp. 117-132, Mar. 10, 2003.

R. Belhassine-Cherif, et al., "Multiple Fault Diagnostics for Communicating Nondeterministic Finite State Machines," 6th IEEE Symposium on Computers and Communications, Jul. 3-5, 2001, pp. 661-666.

M. Ben-Bassat, et al., "A1-Test: A Real Life Expert System for Electronic Troubleshooting (A Description and a Case Study)," 4th Conference on Artificial Intelligence Applications, 1988, pp. 2-10.

F. Brajou, et al., "The Airbus A380—An AFDX-Based Flight Test Computer Concept," 2004 IEEE AUTOTESTCON, pp. 460-463.

Cantone, et al., "IN-ATE: Fault Diagnosis as Expert System Guided Search," Computer Expert Systems, L. Bolc & M.J. Coombs (eds.), Springer-Verlag, New York 1986, pp. 298-348.

"Computerized Diagnostic Tester at Hand," Electrical World, Aug. 1, 1975, pp. 36-38.

T.A. Cross, "A Digital Electronic System for Automobile Testing and Diagnosis," IEE Conference Jul. 6-9, 1976, London, England, pp. 152-159.

eHow Contributor, "How to Organize Computer Files," printed Mar. 31, 2011 from http://www.ehow.com/print/how_138482_organize-computer-files.html.

F. Esposito, et al., "Machine Learning Methods for Automatically Processing Historical Documents: from Paper Acquisition to XML Transformation," 1st Int'l Workshop on Document Image Analysis for Libraries, Jan. 23-24, 2004, pp. 328-335.

H. Garcia-Molina, et al., "dSCAM: Finding Document Copies Across Multiple Databases," 4th Int'l Conference on Parallel and Distributed Information Systems, Dec. 18-20, 1996, pp. 68-79.

I. Ghosh, et al., "Automatic Test Pattern Generation for Functional Register-Transfer Level Circuits Using Assignment Decision Diagrams," IEEE Transactions on Computer-Aided Design of Integrated Circuits and Systems, vol. 20, Issue 3, Mar. 2001, pp. 402-415.

M. Koppel, et al., "Automatically Classifying Documents by Ideological and Organizational Affiliation," IEEE Int'l Conference on Intelligence and Security Informatics, Jun. 8-11, 2009, pp. 176-178.

J.C. Lin, et al., "Using Genetic Algorithms for Test Case Generation in Path Testing," 9th Asian Test Symposium, Dec. 4-6, 2000, pp. 241-246.

W. Linzhang, et al., "Generating Test Cases from UML Activity Diagram Based on Gray-Box Method," 11th Asia-Pacific Software Engineering Conference, Nov. 30-Dec. 3, 2004, pp. 1-8.

B.D. Liu, et al., "Efficient Global Strategy for Designing and Testing Scanned Sequential Circuits," IEE Proceedings on Computers and Digital Techniques, vol. 142, No. 2, Mar. 1995, pp. 170-176.

M. Mayer, "The Computerized Diagnostic Rhyme Test as a Design Tool for Armored Vehicle Intercommunications Systems," Military Communications Conference, 1985, pp. 166-170.

Microsoft at Work, "File Organization tips: 9 ideas for managing files and folders," printed Mar. 30, 2011 from http://www.microsoft.com/atwork/productivity/files.aspx.

(56) References Cited

OTHER PUBLICATIONS

S.M. Namburu, et al., "Systematic Data-Driven Approach to Real-Time Fault Detection and Diagnosis in Automotive Engines," 2006 IEEE AUTOTESTCON, pp. 59-65.

"Names files and folders—How to—Web Team—University of Canterbury, New Zealand," printed on Mar. 31, 2011 from http://www.canterbury.ac.nz/web/how/filename.shtml.

D. Niggemeyer, et al., "Automatic Generation of Diagnostic March Tests," 19th IEEE Proceedings on VLSI Test Symposium, 2001, pp. 299-304.

Yiannis Papadopoulos, et al., "Automating the Failure Modes and Effects Analysis of Safety Critical Systems," Proceedings of the Eighth IEEE Int'l Symposium on High Assurance Systems Engineering (HASE '04), 2004.

F.C. Pembe, et al., "Heading-Based Sectional Hierarchy Identification for HTML Documents," 22nd Int'l Symposium on Computer and Information Sciences, Nov. 7-9, 2007, pp. 1-6.

F. Pipitone, "The FIS Electronics Troubleshooting System Guided Search," Computer Expert Systems, vol. 19, No. 7, 1986, pp. 68-76.

G. Qin, et al., "On-Board Fault Diagnosis of Automated Manual Transmission Control System," IEEE Transactions on Control Systems Technology, vol. 12, No. 4, Jul. 2004, pp. 564-568.

H.M.T. Saarikoski, "2T: Two-Term Indexing of Documents Using Syntactic and Semantic Constraints," 16th Int'l Workshop on Database and Expert Systems Applications, Aug. 22-26, 2005, pp. 1025-1028.

P. Samuel, et al., "UML Sequencing Diagram Based Testing Using Slicing," An Int'l Conference of IEEE India Council, Dec. 11-13, 2005, pp. 176-178.

F.Y. Shih, et al., "A Document Segmentation, Classification and Recognition System," 2nd Int'l Conference on Systems Integration, 1992, pp. 258-267.

Genichi Taguchi, et al., The Mahalanobis-Taguchi System. Published 2000, McGraw-Hill Professional. http://books.google.com/books?id=5AOuyyccV8kC&printsec=frontcover&sig=WdZNGINfzuveQpcYASuCMCvuiO (no hard copy, unable to print, must review on-line).

H. Trier, "Further Development of the Periodical Vehicle Test by Using Diagnostic Interface," IEE Colloquium on Vehicle Diagnostics in Europe, 1994, pp. 4/1-4/2.

J. van Beers, et al., "Test Features of a Core-Based Co-Processor Array for Video Applications," Int'l Test Conference, 1999, pp. 638-647.

J.R. Wagner, "Failure Mode Testing Tool Set for Automotive Electronic Controllers," IEEE Transactions on Vehicular Technology, vol. 43, Issue 1, Feb. 1994, pp. 156-163.

Reuben Wright, et al., "How Can Ontologies Help Repair Your Car?" XTECH 2005: XML, the Web and beyond; May 27, 2005, Amsterdam; http://ww.idealliance.org/proceedings/xtech05/papers/02-07-02/.

* cited by examiner

OPTIMIZING TEST PROCEDURES FOR A SUBJECT UNDER TEST

CROSS REFERENCE TO RELATED APPLICATIONS

This application claims benefit of and is a continuation-in-part of U.S. patent application Ser. No. 11/452,249, entitled "DIAGNOSTIC TEST SEQUENCE OPTIMIZATION METHOD AND APPARATUS," filed Jun. 14, 2006 now U.S. Pat. No. 7,865,278, which is hereby incorporated by reference in its entirety.

FIELD OF THE INVENTION

The present invention relates generally to diagnostic procedures for a subject under test. More particularly, the present invention relates to optimizing the diagnostic procedures for the subject under test.

BACKGROUND OF THE INVENTION

Diagnostic systems are used by technicians and professionals in virtually all industries to perform basic and advanced system testing functions. For example, in the automotive, trucking, heavy equipment and aircraft industries, diagnostic test systems provide for vehicle onboard computer fault or trouble code display, interactive diagnostics, multi-scope and multimeter functions, and electronic service manuals. In the medical industry, diagnostic systems provide for monitoring body functions and diagnosis of medical conditions, as well as system diagnostics to detect anomalies in the medical equipment.

In many industries, diagnostic systems play an increasingly important role in manufacturing processes, as well as in maintenance and repair throughout the lifetime of the equipment or product. Some diagnostic systems are based on personal computer technology and feature user-friendly, menu-driven diagnostic applications. These systems assist technicians and professionals at all levels in performing system diagnostics on a real-time basis.

With the advent of the microprocessor, virtually all modern vehicles have come to utilize onboard computers to control and monitor engine and electrical system functions. Such vehicle onboard computers typically interface with a multiplicity of sensors and transducers, which continuously detect vehicle and engine operational parameters and provide representative electrical signals to the onboard computer. The data collected and processed by the onboard computer can be useful in the diagnosis of vehicle engine and electrical system malfunctions. Thus, the vehicle onboard computer typically includes a communication port connector that allows certain of the collected data to be transmitted to an independent computer analyzer, which may process the data, store the data, or present the data in a visual format that can be interpreted by vehicle maintenance and repair technicians.

In conjunction with these technological developments, a variety of specialized computer analyzers, or vehicle diagnostic tools, have been developed and marketed to provide vehicle maintenance and repair technicians access to the data available from the vehicle onboard computers. The current technology includes a variety of hand-held vehicle diagnostic tools, frequently referred to as scan tools, with considerable processing capabilities, typically incorporating an integral display and capable of displaying the onboard computer data in a variety of graphical formats that allow vehicle technicians to view and interpret the data.

The diagnostic procedures for diagnostic systems utilizing equipment this sort are typically developed by experienced technical experts or professionals. The technical expert or professional provides the technical experience and knowledge required to develop complex diagnostic procedures. Thus, the efficacy of the diagnostic procedures, in particular the sequence in which the diagnostic procedures are performed, is highly dependent on the expertise of the technical expert or professional authoring the procedures. The diagnostic procedures for diagnostic systems of this sort are typically developed by experienced technical experts or professionals. The technical expert or professional provides the technical experience and knowledge required to develop complex diagnostic procedures. Thus, the efficacy of the diagnostic procedures, in particular the sequence in which the diagnostic procedures are performed, is highly dependent on the expertise of the technical expert or professional authoring the procedures.

Thus, existing diagnostic systems have a disadvantage in that the sequence of execution of diagnostic procedures is highly dependent upon the expertise of the technical experts and professionals who author the diagnostic procedures. The technical experts and professionals often do not have access to complete information regarding historical outcomes of diagnostic testing that has been performed, and in particular, statistical information regarding the historical outcomes of diagnostic testing. As a result, diagnostic testing can consume unnecessary time and cost, because it is based on incomplete information. Accordingly, it is desirable to provide a method and apparatus for optimizing the sequence of diagnostic test procedures that can be executed on diagnostic systems, such as a medical diagnostic systems.

SUMMARY OF THE INVENTION

The foregoing needs are met, to a great extent, by the present invention, wherein in one aspect an apparatus and method are provided that in some embodiments provide for optimizing the diagnostic procedures for the subject under test at least to some extent.

An embodiment of the present invention pertains to a computer-implemented method of optimizing a diagnostic test sequence to diagnose a medical condition of a subject. The method includes the steps of: determining a group of diagnostic tests related to a symptom of the subject from a pool of diagnostic tests; conducting a probabilistic medical condition analysis determining the efficacy of each of the diagnostic tests based on historical outcomes of actual diagnostic testing; analyzing a comparative utility of each diagnostic tests based on a plurality of factors that can affect a problem resolution; assigning a weight to each factor involved in the probabilistic medical condition analysis; ordering the diagnostic tests based upon at least one of: a probability of the diagnostic test identifying a cause of the medical condition in a minimum amount of time; a probability of the diagnostic test identifying the cause of the medical condition at a minimum cost; and a relative weighting of minimizing time versus minimizing cost; and selecting a first diagnostic test from the group based at least in part on the probabilistic medical condition analysis and the weighted factors involved therein.

Another embodiment of the present invention relates to a diagnostic tool for optimizing a diagnostic test sequence to diagnose a medical condition of a subject. The diagnostic tool includes: a diagnostic test selector configured to determine a group of diagnostic tests related to a symptom of the subject from a pool of diagnostic tests; a medical condition analyzer configured to determine the efficacy of each of the diagnostic tests of the group based on historical outcomes of actual diagnostic testing via a probabilistic medical condition analysis; an analyzer configured to analyze a comparative utility of each diagnostic tests of the group based on a plurality of factors that can affect a problem resolution; a weighter configured to assign a weight to each factor involved in the probabilistic medical condition analysis; an orderer configured to order the group diagnostic tests based upon at least one of a probability of the diagnostic test identifying a cause of the medical condition in a minimum amount of time; a probability of the diagnostic test identifying the cause of the medical condition at a minimum cost; and a relative weighting of minimizing time versus minimizing cost; and a sequence optimizer configured to select a first diagnostic test from the group based at least in part on a probabilistic medical condition analysis and the weighted factors involved therein.

Yet another embodiment of the present invention pertains to a diagnostic tool for optimizing a diagnostic test sequence to diagnose a medical condition of a subject. The diagnostic tool includes: a diagnostic test selector configured to determine a group of diagnostic tests related to a symptom of the subject from a pool of diagnostic tests; a sequence optimizer configured to select a first diagnostic test from the group based at least in part on a probabilistic medical condition analysis, the probabilistic medical condition analysis being based on historical outcomes of actual diagnostic testing; a medical condition analyzer configured to quantify a comparative utility of an individual diagnostic test of the group based on a plurality of factors that can affect a problem resolution; a factor weighter configured to assign a weight to each of a plurality of probabilistic medical condition analysis factors; and a medical history receiver configured to receive a medical history of the subject, wherein the probabilistic medical condition analyzer is further configured to base the comparative utility at least in part on the medical history.

In still another embodiment, the present invention relates to a computer-implemented method of optimizing a diagnostic test sequence to diagnose a medical condition of a subject. The method includes the steps of: determining a group of diagnostic tests related to a symptom of the subject from a pool of diagnostic tests; optimizing an order of the group of diagnostic tests, the optimization comprising: conducting a probabilistic medical condition analysis to determine the efficacy of each of the diagnostic tests of the group based on historical outcomes of actual diagnostic testing; analyzing a comparative utility of each diagnostic tests of the group based on a plurality of factors that can affect a problem resolution; assigning a weight to each factor involved in the probabilistic medical condition analysis; selecting a first diagnostic test from the group; and iteratively optimizing the order of the group of diagnostic tests in response to prompting by an intermediate diagnostic test information being received.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

An embodiment of the present inventive method and apparatus can provide a diagnostic test sequence optimizer that can determine a group of individual diagnostic tests, or procedures, related to a symptom from a pool of diagnostic procedures to diagnose a failure mode of a subject under test. In some embodiments, the subject may include a vehicle, computer network, person, or animal, and the like. The diagnostic test sequence optimizer can also include a failure mode analyzer that can quantify a comparative utility of the individual diagnostic tests, as well as a factor weighter that can assign a weight to each of a number of individual factors that can be figured into the failure mode analysis. In a particular embodiment described with reference to FIGS. 1-3, the subject under test is a vehicle or other machine, however, in other examples described herein, the subject under test may include a patient, computer system, etc.

Figure 1:
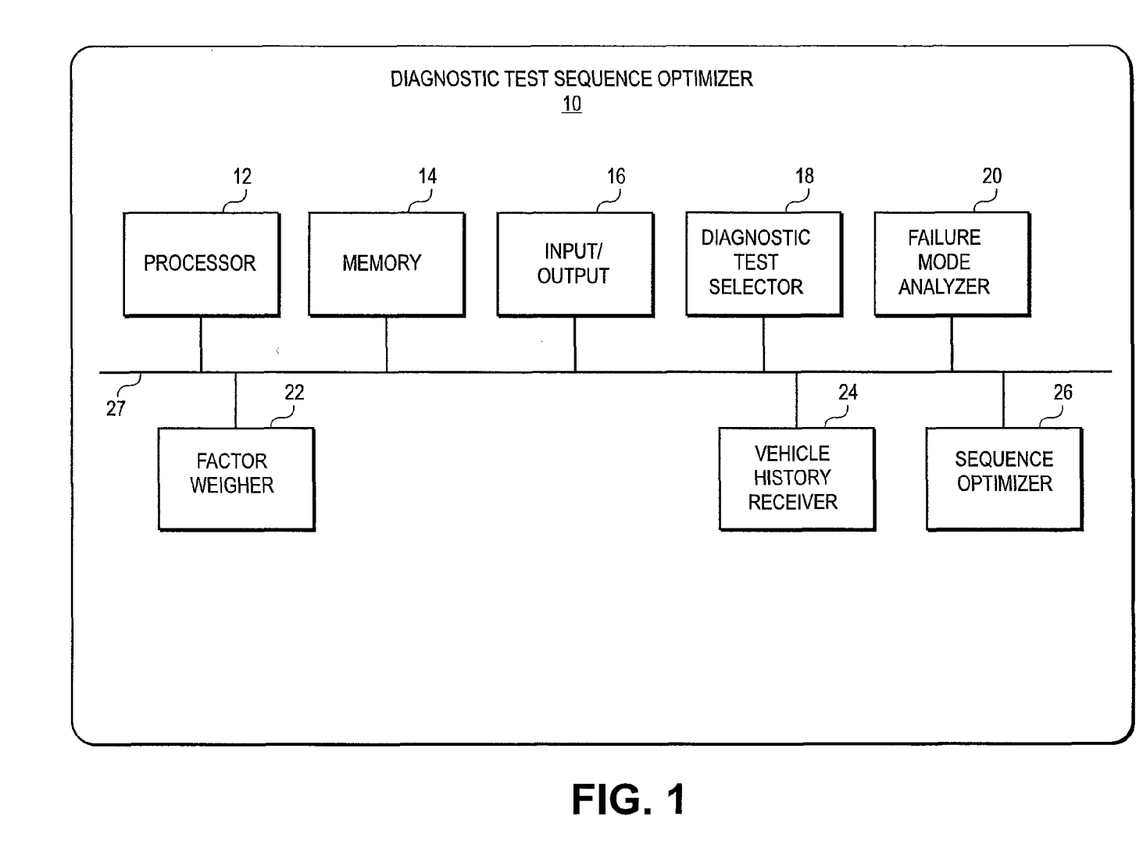
FIG. 1 is a schematic diagram illustrating a diagnostic test sequence optimizer according to an embodiment of the invention.

The diagnostic test sequence optimizer can further include a vehicle history receiver that can receive information regarding the maintenance and repair history of the vehicle under test, which can also be factored into the failure mode analysis. The diagnostic test sequence optimizer can also include a sequence optimizer that can arrange the order the diagnostic tests in accordance with the individual comparative utilities of the tests and other significant factors. In addition, the failure mode analyzer and the sequence optimizer can take into account user preferences to further optimize the diagnostic test sequence.

An embodiment of the diagnostic test sequence optimizer can complement or can be an integral part of a diagnostic test procedure generator. An example of a diagnostic test procedure generator that is compatible with the interactive diagnostic schematic generator is disclosed in copending U.S.

Patent Application, entitled "Diagnostic Decision Sequencing Method and Apparatus for Optimizing a Diagnostic Test Plan," filed concurrently herewith by Fountain, et al., the disclosure of which is hereby incorporated by reference in its entirety.

The invention will now be described with reference to the drawing figures, in which like reference numerals refer to like parts throughout. An embodiment of the present inventive apparatus and method is illustrated in FIG. 1, which illustrates a diagnostic test sequence optimizer 10. The diagnostic test sequence optimizer 10 can produce a vehicle diagnostic test sequence for use with, for example, a PC-based vehicle diagnostic system to provide instructions for expert diagnostic procedures to allow a vehicle technician to identify the cause of a trouble code or operational problem at the component level.

An example of a diagnostic method for use with a vehicle diagnostic system of this type is disclosed in U.S. Pat. No. 5,631,831, entitled "Diagnosis Method For Vehicle Systems," to Bird, et al., dated May 20, 1997, the disclosure of which is hereby incorporated by reference in its entirety. The diagnostic test sequence can navigate a vehicle technician through a step-by-step test sequence based on a vehicle onboard computer trouble code or a vehicle operational symptom. For example, during vehicle diagnostics, test step instructions and related information can be displayed to the vehicle technician on a display screen panel.

Diagnostic procedures can be authored, for example, by an expert vehicle technician, and subsequently ordered in an optimal sequence by the diagnostic test sequence optimizer 10. An example of a method for authoring diagnostic procedures for use with a vehicle diagnostic system is disclosed in U.S. patent application Ser. No. 11/052,118, filed by Fountain, et al. on Feb. 8, 2005, the disclosure of which is hereby incorporated by reference in its entirety.

The diagnostic test sequence optimizer 10 can include a processor 12, a memory 14, an input/output device 16, a diagnostic test selector 18, a failure mode analyzer 20, a factor weighter 22, a vehicle history receiver 24 and a sequence optimizer 26, all of which can be interconnected by a data bus 27. The processor 12, the memory 14, the input/output device 16 and the display device (not shown) can be part of a general computer, such as a personal computer (PC), a notebook, a UNIX workstation, a server, a mainframe computer, a personal digital assistant (PDA), or some combination of these. Alternatively, the processor 12, the memory 14 and the input/output device 16 can be part of a specialized computing device, such as a vehicle diagnostic scan tool. The remaining components can include programming code, such as source code, object code or executable code, stored on a computer-readable medium that can be loaded into the memory 14 and processed by the processor 12 in order to perform the desired functions of the diagnostic test sequence optimizer 10.

In various embodiments, the diagnostic test sequence optimizer 10 can be coupled to a communication network, which can include any viable combination of devices and systems capable of linking computer-based systems, such as the Internet; an intranet or extranet; a local area network (LAN); a wide area network (WAN); a direct cable connection; a private network; a public network; an Ethernet-based system; a token ring; a value-added network; a telephony-based system, including, for example, T1 or E1 devices; an Asynchronous Transfer Mode (ATM) network; a wired system; a wireless system; an optical system; a combination of any number of distributed processing networks or systems or the like.

An embodiment of the diagnostic test sequence optimizer 10 can be coupled to the communication network by way of the local data link, which in various embodiments can incorporate any combination of devices—as well as any associated software or firmware—configured to couple processor-based systems, such as modems, network interface cards, serial buses, parallel buses, LAN or WAN interfaces, wireless or optical interfaces and the like, along with any associated transmission protocols, as may be desired or required by the design.

Additionally, an embodiment of the diagnostic test sequence optimizer 10 can communicate information to the user and request user input by way of an interactive, menu-driven, visual display-based user interface, or graphical user interface (GUI). The user interface can be executed, for example, on a personal computer (PC) with a mouse and keyboard, with which the user may interactively input information using direct manipulation of the GUI. Direct manipulation can include the use of a pointing device, such as a mouse or a stylus, to select from a variety of selectable fields, including selectable menus, drop-down menus, tabs, buttons, bullets, checkboxes, text boxes, and the like. Nevertheless, various embodiments of the invention may incorporate any number of additional functional user interface schemes in place of this interface scheme, with or without the use of a mouse or buttons or keys, including for example, a trackball, a touch screen or a voice-activated system.

The diagnostic test selector 18 can determine a group of diagnostic tests that are related to or based on a symptom of a vehicle operational fault or an onboard computer trouble code. The determination can be based, for example, on a diagnostic Failure Mode and Effects Analysis (FMEA) or on an author priority setting.

A FMEA, or equivalently, a Failure Mode and Effects Criticality Analysis (FMECA), is a widely used tool in manufacturing industries, for example, the aerospace industry, the automotive industry, the heavy equipment industry and the digital electronics industry. A typical FMEA can include a list of failure modes and causes, effects associated with each of the failure modes, a severity of each failure mode, a risk or probability of the occurrence of each failure mode and additional information that can be useful in designing and manufacturing the associated product. For example, the FMEA can include estimated probability information based on engineering analysis or statistical probability estimates based on empirical data from actual failures. Thus, each diagnostic test procedure can be an individual failure mode test based on the failure modes identified in the FMEA, and the FMEA information can be used to determine which of the diagnostic test procedures is most likely to identify the cause of the symptom.

The FMEA or probability information available to the diagnostic test sequence optimizer 10 can be updated periodically with new estimates or empirical vehicle fleet failure mode information, for example, from a central database maintained by a service center or the vehicle manufacturer. Thus, the FMEA or probability information can be automatically updated, for example, over a communication network.

Some existing diagnostic test systems include sequences of diagnostic test procedures that can performed on a vehicle or other product to determine a cause of a symptom. However, in some existing systems the sequence of the diagnostic tests is determined based solely on the priority assigned by an expert diagnostic author. An embodiment of the present invention can have the advantage that the diagnostic test procedure sequence can be optimized using statistical probability information based on historical outcomes of actual diagnostic testing in order to more accurately determine the efficacy of each of the diagnostic procedures. As a result, the diagnostic test procedure sequence can be customized to minimize or optimize the time required to resolve the problem, the cost required to resolve the problem, additional factors that can affect the problem resolution, a combination of these factors, or the like.

The failure mode analyzer 20 can perform an analysis of the comparative utility of each of the individual diagnostic procedures based on a number of different factors that can affect problem resolution. For example, the failure mode analysis factors can include one or more of the following:

an estimated time required to perform a diagnostic test;
   the difficulty of performing the diagnostic test;
   an estimated time required to remove and replace a component associated with the diagnostic test;
   the difficulty of removing and replacing the component;
   the level of expertise of a vehicle service technician performing the diagnostic procedure;
   the availability of a replacement component;
   the estimated cost or the actual cost of the component;
   the estimated or actual cost of labor;
   empirical data regarding the probability that a failure mode associated with the individual diagnostic procedure exists given the existence of a specified symptom (e.g., FMEA data);
   an estimate of the probability that the failure mode exists given the existence of the symptom;
   a frequency or rate of the failure mode associated with the diagnostic procedure;
   the mileage of the subject vehicle;
   the specific configuration of the vehicle or a modification that has been performed on the vehicle;
   the vehicle maintenance record;
   a service center maintenance record regarding the vehicle or associated vehicles;
   a manufacturer warranty record associated with the specific vehicle or a type of vehicle;
   a recommended maintenance schedule, such as a manufacturer recommended maintenance schedule; or
   a technical service bulletin issued by the vehicle manufacturer.

In addition, the factor weighter 22 can assign a weight or weighting to each of the factors used in the failure mode analysis. For example, a heavier weighting can be given to the time required to perform an individual diagnostic procedure versus the cost of performing the procedure and replacing an associated component, or vice-versa. Similarly, a greater weight can be assigned to the difficulty of performing the diagnostic procedure, for example, in relation to the expertise level of the vehicle technician. In other cases, a greater weighting may be placed on the availability of a replacement component. For example, a diagnostic procedure related to a component that is not available may be given a particularly low weighting. In yet other cases, a heavier weighting can be assigned to a diagnostic procedure associated with a recommended maintenance procedure that is coming due, for example, based on the vehicle mileage, and has not been performed on the subject vehicle. Similarly, a heavy weighting can be placed on a diagnostic procedure related to a technical service bulletin, such as a recommended technical service bulletin issued by the vehicle manufacturer.

Furthermore, the weights can be partially determined based on user preferences. For example, a user preference setting can be set by a diagnostic procedure author, by a service center or by a vehicle technician, and subsequently factored into the individual weightings of the factors. For example, a service center or a vehicle technician may prefer to minimize either time or cost, depending on the vehicle type, customer feedback or the like. Thus, a user input, for example, received via the input/output device 16, can be used by the factor weighter 22 in determining the weightings of certain critical factors in accordance with user preferences.

The vehicle history receiver 24 can receive a history of the vehicle, for example, a maintenance or repair record kept with the vehicle, at a service center, or by the manufacturer. For example, the vehicle history can include information such as the mileage on the subject vehicle, the specific configuration of the vehicle, a modification such as a from technical service bulletin that has been performed on the vehicle, a vehicle maintenance record, a service center maintenance record associated with the specific vehicle or type of vehicle, or a manufacturer warranty record associated with the specific vehicle or type of vehicle.

Accordingly, the sequence optimizer 26 can use the outcome from the failure mode analysis performed by the failure mode analyzer 20, the vehicle history received by the vehicle history receiver 24, user settings received by way of user input, a diagnostic FMEA or other input factors to arrange, or order, the diagnostic test procedures in a sequence. The sequence can be optimized in accordance with the priority input by a diagnostic test procedure author, a user preference input and any combination of the failure mode analysis factors. Thus, the sequence optimizer 26 is highly configurable to allow customization of the sequence optimization process.

For example, the diagnostic test procedures can be ordered according to the probability of identifying a specific cause of a symptom in a minimum amount of time. As another example, the diagnostic test sequence can be optimized according to the probability of identifying the cause of the symptom with a minimum cost. Additionally, the diagnostic test sequence can be optimized according to a relative weighting of the importance of minimizing time versus minimizing cost. Thus, the sequence optimizer 26 can be configured to optimize the diagnostic test sequence in accordance with any desired combination of priorities or preferences.

In addition, in some embodiments of the diagnostic test sequence optimizer 10, the diagnostic test procedures can be ordered based on multiple symptoms. For example, the failure mode analyzer 20 can evaluate two or more simultaneously occurring or intermittent symptoms in order to identify a possible common cause. Accordingly, the sequence optimizer 26 can dynamically reorder the test procedure sequence during test execution based on an interrelation of two or more symptoms. For example, failure mode analyzer 20 may identify a common voltage source for two sensors that simultaneously have symptoms, and the sequence optimizer 26 can reorder the test sequence to verify the functionality of the common voltage source before performing failure mode tests on the individual sensors. Once again, the test sequence can also be based on the comparative failure rates of the individual sensors and the common voltage source.

Moreover, in some embodiments of the diagnostic test sequence optimizer 10, the sequence optimizer 26 can dynamically reorder the test sequence during test execution based on intermediate results, for example, based on the results of a particular failure mode test or a combination of failure mode tests. For example, even though a particular failure mode test does not result in a final diagnosis, the failure mode test, alone or in combination with one or more other failure mode tests, can validate the correct functionality of a component. As a result, the sequence optimizer 26 can dynamically reorder the test sequence, for example, to omit further failure mode tests corresponding the validated component, or to move remaining failure mode tests corresponding the validated component to a later position of lesser priority in the test sequence.

Similarly, in some embodiments of the diagnostic test sequence optimizer 10, the sequence optimizer 26 can dynamically reorder the test sequence during diagnostic test execution based on new information derived from a particular failure mode test, although the failure mode test does not result in a final diagnosis. For example, the discovery of an additional symptom during a particular failure mode test can result in the sequence optimizer 26 modifying the test sequence based on the interrelation of the newly discovered symptom and the previously known symptom or symptoms. Thus, the sequence optimizer 26 can perform iterative, dynamic, run-time reevaluations during diagnostic test execution to continually modify or recreate the test sequence.

Moreover, the diagnostic test sequence optimizer 10 can be combined with additional diagnostic system capabilities, such as vehicle state tracking, a graphical user interface and interactive diagnostic schematics, to form an intelligent diagnostic system that can aid vehicle technicians in resolving vehicle operational problems in an optimized manner For example, the current vehicle state can be used in optimizing the diagnostic test sequence. That is to say, preconditions required for a diagnostic procedure such as cover panels or components that are removed or modified during individual diagnostic procedures, test equipment that is connected to the vehicle, and similar such information related to the vehicle state can be used by the sequence optimizer 26 to determine the diagnostic test sequence.

Figure 2:
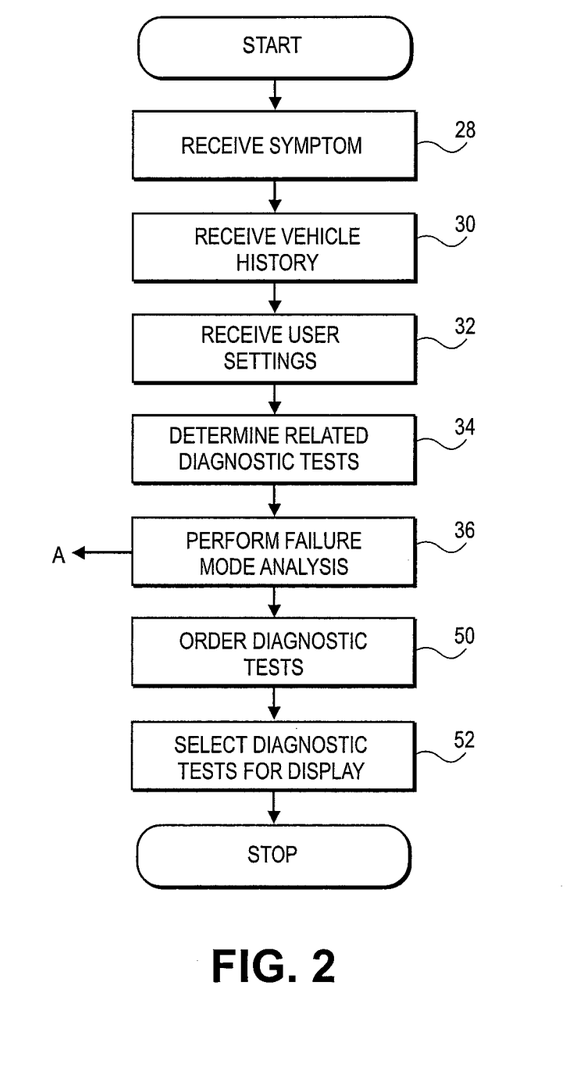
FIG. 2 is a flow chart illustrating steps that may be followed in accordance of one embodiment of the method or process of optimizing a diagnostic test sequence.

FIG. 2 illustrates a method or process for optimizing a diagnostic test sequence. The process can begin by proceeding to step 28, "RECEIVE SYMPTOM," in which a symptom such as a vehicle operational problem or a diagnostic trouble code can be received for diagnosis to identify a failure mode of a vehicle. Next, in step 30, "RECEIVE VEHICLE HISTORY," history information regarding a specific test subject vehicle can be received, such as vehicle mileage, vehicle configuration, vehicle modifications, maintenance record or warranty record. Then, in step 32, "RECEIVE USER SETTINGS," a user preference input can be received.

Control then passes to step 34, "DETERMINE RELATED DIAGNOSTIC TESTS," in which diagnostic tests, or procedures, that are related to the symptom and vehicle type can be identified from a pool of diagnostic tests. The diagnostic tests can be, for example, authored by an expert diagnostic technician, or converted from an existing fault tree or a diagnostic FMEA. Each of the diagnostic test procedures can be associated with a specific failure mode of a vehicle component.

Figure 3:
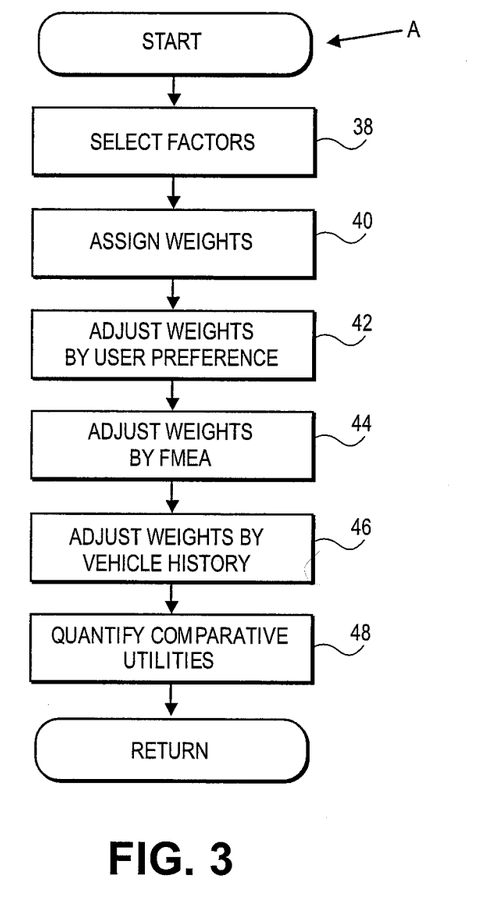
FIG. 3 is a flow chart illustrating steps that may be followed to perform a failure mode analysis that is compatible with the method of FIG. 2.

At this point, in step 36, "PERFORM FAILURE MODE ANALYSIS," a comparative utility of each of the individual diagnostic test procedures can be quantified. FIG. 3 illustrates a method or process for performing a failure mode analysis. In step 38, "SELECT FACTORS," one or more factors that can affect the resolution of a failure mode can be selected for use in the analysis, as described above. Next, in step 40, "ASSIGN WEIGHTS," a weight, or weighting, can be assigned to each of the selected factors in accordance with a priority or preference representing the relative importance of each of the factors with regard to remaining factors.

Control then passes to step 42, "ADJUST WEIGHTS BY USER PREFERENCE," in which each of the weights can be adjusted to reflect a user preference setting, as described above. Next, in step 44, "ADJUST WEIGHTS BY FMEA," each of the weights can be adjusted to reflect the information, such as probability or risk factors from the FMEA, as described above. In turn, in step 46, "ADJUST WEIGHTS BY VEHICLE HISTORY," each of the weights can be adjusted in accordance with the vehicle history, such as a recommended maintenance procedure that is coming due and has not been performed on the vehicle, as described above.

Subsequently, in step 48, "QUANTIFY COMPARATIVE UTILITIES," the weighted factors can be used in an algorithm to determine a numerical comparative utility for each of the diagnostic test procedures. For example, the comparative utility can reflect the likelihood that the test procedure will result in resolution of the problem taking into account the time and cost required to perform the diagnostic procedure.

Returning to FIG. 2, in step 50, "ORDER DIAGNOSTIC TESTS," the diagnostic test procedures can be placed in an order that optimizes the overall utility of the diagnostic test sequence. That is, the diagnostic test procedures can be placed in a sequence that optimizes selected factors in accordance with user preferences and the vehicle history, or other desired factors, as described above.

At this point, in step 52, "SELECT DIAGNOSTIC TESTS FOR DISPLAY," a subset of the diagnostic tests can optionally be selected for display on a display device. Thus, the optimized sequence of diagnostic test procedures can be presented to a vehicle technician to aide the vehicle technician in diagnosing a failure mode associated with a vehicle system.

FIGS. 1-6 are block diagrams and flowcharts of methods, apparatuses and computer program products according to various embodiments of the present invention. It will be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus according to the present invention can include other means, such as hardware or some combination of hardware and software, including one or more processors or controllers, for performing the disclosed functions.

Figure 4:
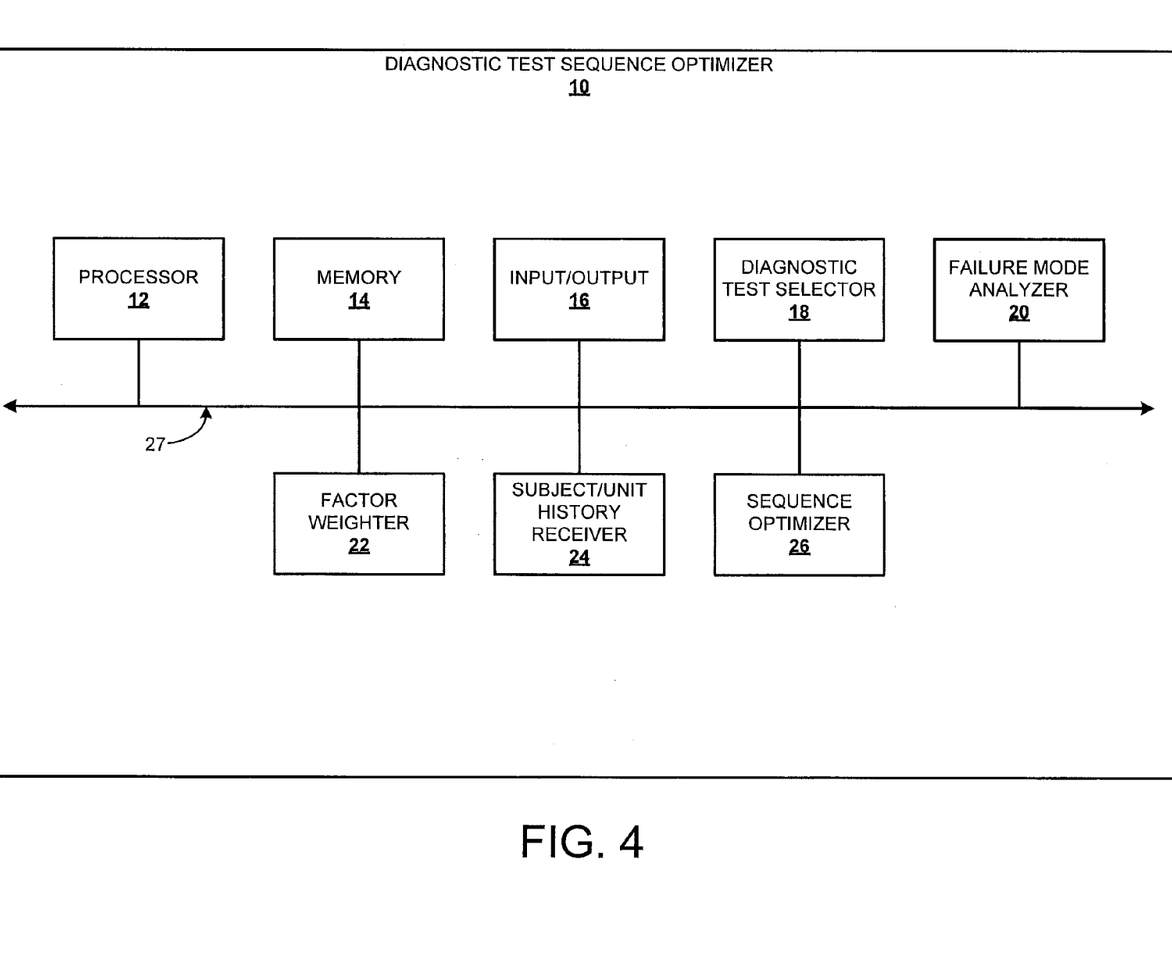
FIG. 4 is a schematic diagram illustrating a diagnostic test sequence optimizer according to another embodiment of the invention.

In this regard, FIGS. 1 and 4 depict the apparatus of various embodiments including several of the key components of a general-purpose computer by which an embodiment of the present invention may be implemented. Those of ordinary skill in the art will appreciate that a computer can include many more components than those shown in FIGS. 1 and 4. However, it is not necessary that all of these generally conventional components be shown in order to disclose an illustrative embodiment for practicing the invention. The general-purpose computer can include a processing unit 12 and a system memory 14, which may include random access memory (RAM) and read-only memory (ROM). The computer also may include nonvolatile storage memory, such as a hard disk drive, where additional data can be stored.

An embodiment of the present invention can also include one or more input or output devices 16, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

Typically, computer program instructions may be loaded onto the computer or other general purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Another embodiment of the diagnostic test sequence optimizer 10 is illustrated in FIG. 4. The diagnostic test sequence optimizer 10 of FIG. 4 is similar to the embodiment of FIG. 1 and thus, for the sake of brevity, those elements already described hereinabove will not be described again. The diagnostic test sequence optimizer 10 may be configured to produce a subject diagnostic test sequence for use with, for example, a computer based subject diagnostic system to provide instructions for expert diagnostic procedures to allow a subject technician (doctor, nurse, veterinarian, and similar medical or animal specialists) to identify the cause of a medical condition in a subject (e.g., a human or animal patient) or a technician (mechanic and the like) operational problem with a unit (e.g., a device or component of the device). For the purpose of this disclosure, the term 'subject' refers to any suitable living being such as a human, pet, livestock, or other such animal. The term, 'unit' as used herein refers to any suitable device such as a refrigeration device or component, a machine, computer or computer system, and the like. The example embodiments below will be explained mainly related to a subject but it can be understood that equivalent or similar example embodiments can be made for a unit.

The diagnostic test sequence can navigate a subject/unit technician through a step-by-step test sequence based on symptoms (fever, headache, deteriorating organs, itching, running nose, coughing, etc.) or medical history (high blood pressure, high cholesterol, alcohol abuse, gout, etc.) of the subject. For example, during subject diagnostics, test step instructions and related information can be displayed to the subject technician on a display screen panel. Diagnostic procedures can be authored, for example, by an expert subject technician such as a doctor, medical professors or other qualified medical personnel (e.g., who are medically licensed), and subsequently ordered in an optimal sequence by the diagnostic test sequence optimizer 10.

The diagnostic test sequence optimizer 10 can include the processor 12, the memory 14, the input/output device 16, the diagnostic test selector 18, the failure mode analyzer 20 (e.g. medical condition), the factor weighter 22, a subject history receiver 24 and the sequence optimizer 26, all of which can be interconnected by the data bus 27. The processor 12, the memory 14, the input/output device 16 and the display device (not shown) can be part of a general computer, such as a personal computer (PC), a notebook, a UNIX workstation, a server, a mainframe computer, a personal digital assistant (PDA), a tablet, or some combination of these. Alternatively, the processor 12, the memory 14 and the input/output device 16 can be part of a specialized computing device, such as a medical imaging device (x-ray, CAT scan, MRI, etc.), medical testing equipment (measures blood pressure, cell count, cholesterol, cardiac output, uric acid levels, etc.), other medical diagnostic tool, and the like. The remaining components can include programming code, such as source code, object code or executable code, stored on a computer-readable medium that can be loaded into the memory 14 and processed by the processor 12 in order to perform the desired functions of the diagnostic test sequence optimizer 10.

An embodiment of the diagnostic test sequence optimizer 10 can be coupled to the communication network by way of the local data link, as described herein. Additionally, an embodiment of the diagnostic test sequence optimizer 10 can communicate information to the user (such as a medical professional, technician, nurse, etc.) and request user input by way of an interactive, menu-driven, visual display-based user interface, or graphical user interface (GUI), as described herein.

The diagnostic test selector 18 can determine a group of diagnostic tests that are related to or based on a symptom of a subject or other indications. For medical or patient diagnostic tests, the determination may be based upon generally known physician references and databases of symptoms and the associated medical tests. For units or devices, the determination can be based, for example, on a diagnostic Failure Mode and Effects Analysis (FMEA) or on an author priority setting as described herein.

Some existing diagnostic test systems include sequences of diagnostic test procedures that can performed on a subject or other product to determine a cause of a symptom. However, in some existing systems the sequence of the diagnostic tests is determined based solely on the priority assigned by an expert diagnostic author. An embodiment of the present invention can have the advantage that the diagnostic test procedure sequence can be optimized using statistical probability information based on historical outcomes of actual diagnostic testing (on patients, animals, etc.) in order to more accurately determine the efficacy of each of the diagnostic procedures. As a result, the diagnostic test procedure sequence can be customized to minimize or optimize the time required to resolve the problem, the cost required to resolve the problem, additional factors that can affect the problem resolution, a combination of these factors, or the like.

The failure mode analyzer 20 (e.g. medical condition analyzer) can perform an analysis of the comparative utility of each of the individual diagnostic procedures based on a number of different factors that can affect a problem resolution as described herein. For example:

an estimated time required to perform a diagnostic test;

the difficulty of performing the diagnostic test;

the availability of a room (e.g. surgery room, outpatient room) and the associated equipments (surgical, x-rays) to perform the diagnostic test;

an estimated time required to remove and replace a component (e.g., organs, prosthetic limb);

the level of difficulty for removing and replacing the component;

the level of expertise of a technician (transplant surgeon, radiologists, cardiologists, etc.) performing the diagnostic procedure;

the availability of a replacement component (organ donor available, prosthetic limb that fits, etc.);

the estimated cost or the actual cost of the component;

the estimated or actual cost of labor and the amount that will be reimbursed by any medical insurance or medicare/medicaid;

empirical data regarding the probability that a failure mode (e.g. medical condition) associated with the individual diagnostic procedure exists given the existence of a specified symptom (rejection of the organ, pain in foot due to high levels of uric acid, high blood pressure, etc.);

an estimate of the probability that the failure mode exists given the existence of the symptom (high white blood cell count, high cholesterol, high uric acid levels, etc.);

a frequency or rate of the failure mode (rejection of organ, pain in chest, etc.) associated with the diagnostic procedure;

the age of the subject and other previous surgeries or treatments;

the subject's medical history and record;

health coverage of the subject, if any;

advance directive in place (living will etc.);

a recommended testing schedule (mammogram, annual physical, etc.); or a bulletin issued by the American Medical Association or Food and Drug Administration or any recognized medical or governmental institutions and the like.

Furthermore, the factor weighter 22 can assign a weight or weighting to each of the factors used in the failure mode analysis. For example, a heavier weighting can be given to the time required to perform an individual diagnostic procedure versus the cost of performing the procedure and replacing an associated component (organ, artificial limb, etc.), or vice-versa. Similarly, a greater weight can be assigned to the difficulty of performing the diagnostic procedure, for example, in relation to the expertise level (advance training, fellowship in the area of specialty, etc.) of the subject technician. In other cases, a greater weighting may be placed on the availability of a replacement component (organ donor available, artificial limb that fits, etc.). For example, a diagnostic procedure related to a component that is not available may be given a particularly low weighting. In yet other cases, a heavier weighting can be assigned to a diagnostic procedure associated with a recommended maintenance procedure (mammogram, annual checkup, etc.) that is coming due, for example, based on the subject's age, and has not been performed on the subject. Similarly, a heavy weighting can be placed on a diagnostic procedure related to a bulletin, such as a recommended medical procedure issued by the AMA or FDA.

Moreover, the weights can be partially determined based on user preferences. For example, a user preference setting can be set by a medical professional, diagnostic procedure author, by a hospital or medical center or by a subject technician, and subsequently factored into the individual weightings of the factors. For example, a hospital, health maintenance organization (HMO), medical center or a subject technician may prefer to minimize either time or cost, depending on the subject, feedback or the like. Thus, a user input, for example, received via the input/output device 16, can be used by the factor weighter 22 in determining the weightings of certain critical factors in accordance with user preferences.

The subject history receiver 24 can receive a medical history of the subject, for example, medical records, family history of disease, results of genetic or other such testing, and the like.

Accordingly, the sequence optimizer 26 can use the outcome from the failure mode analysis performed by the failure mode analyzer 20, the subject history received by the subject history receiver 24, user settings received by way of user input, a diagnostic statistical analysis or other input factors to arrange, or order, the diagnostic test procedures in a sequence. The sequence can be optimized in accordance with the priority input by a diagnostic test procedure author, a user preference input and any combination of the failure mode analysis factors. Thus, the sequence optimizer 26 is highly configurable to allow customization of the sequence optimization process.

For example, the diagnostic test procedures can be ordered according to the probability of identifying a specific cause (medical in the event of a subject or technical in the event of the unit) of a symptom (medical or hardware failure, etc.) in a minimum amount of time. As another example, the diagnostic test sequence can be optimized according to the probability of identifying the cause (medical in the event of a subject or technical in the event of the unit) of the symptom with a minimum cost. Additionally, the diagnostic test sequence can be optimized according to a relative weighting of the importance of minimizing time versus minimizing cost. Thus, the sequence optimizer 26 can be configured to optimize the diagnostic test sequence in accordance with any desired combination of priorities or preferences.

In addition, in some embodiments of the diagnostic test sequence optimizer 10, the diagnostic test procedures can be ordered based on multiple symptoms. For example, the failure mode analyzer 20 can evaluate two or more simultaneously occurring or intermittent symptoms in order to identify a possible common cause. Accordingly, the sequence optimizer 26 can dynamically reorder the test procedure sequence during test execution based on an interrelation of two or more symptoms.

Moreover, in some embodiments of the diagnostic test sequence optimizer 10, the sequence optimizer 26 can dynamically reorder the test sequence during test execution based on intermediate results, for example, based on the results of a particular failure mode test (or medical diagnostic tests) or a combination of failure mode tests. For example, even though a particular failure mode test does not result in a final diagnosis, the failure mode test, alone or in combination with one or more other failure mode tests, can validate the correct functionality of an organ. As a result, the sequence optimizer 26 can dynamically reorder the test sequence, for example, to omit further failure mode tests corresponding the working organ, or to move remaining failure mode tests corresponding the working organ to a later position of lesser priority in the test sequence.

Similarly, in some embodiments of the diagnostic test sequence optimizer 10, the sequence optimizer 26 can dynamically reorder the test sequence during diagnostic test execution based on new information derived from a particular failure mode test, although the failure mode test does not result in a final diagnosis. For example, the discovery of an additional symptom during a particular failure mode test can result in the sequence optimizer 26 modifying the test sequence based on the interrelation of the newly discovered symptom and the previously known symptom or symptoms. Thus, the sequence optimizer 26 can perform iterative, dynamic, run-time reevaluations during diagnostic test execution to continually modify or recreate the test sequence.

Moreover, the diagnostic test sequence optimizer 10 can be combined with additional diagnostic system capabilities, such as subject/unit state tracking, a graphical user interface and interactive diagnostic schematics, to form an intelligent diagnostic system that can aid subject/unit technicians in resolving subject/unit operational problems in an optimized manner For example, the current subject/unit state can be used in optimizing the diagnostic test sequence. In medical diagnostic testing, this may result in having two or more procedures performed at one time, such as biopsies, to reduce patient trauma and/or accelerate the diagnosis process.

Figure 5:
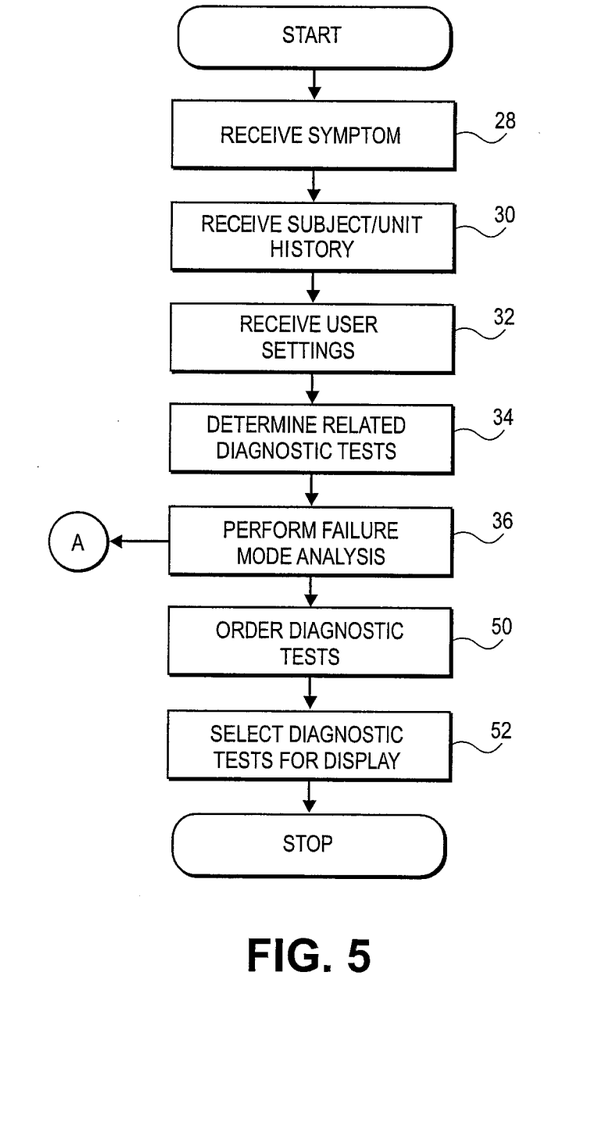
FIG. 5 is a flow chart illustrating steps that may be followed in accordance with the embodiment of FIG. 4 of the method or process of optimizing a diagnostic test sequence.

FIG. 5 illustrates a method or process for optimizing a diagnostic test sequence. The method is similar or the same as the method shown in FIG. 2 with the exception that the subject under test includes medical patients and devices beyond vehicles. The process can begin by proceeding to step 28, "RECEIVE SYMPTOM," in which a symptom such as a subject/unit operational problem or a code can be received for diagnosis to identify a failure mode of a subject/unit. Next, in step 30, "RECEIVE SUBJECT/UNIT HISTORY," history information regarding the medical history of the subject. Then, in step 32, "RECEIVE USER SETTINGS," a user preference input can be received. The user preferences are previously discussed.

Control then passes to step 34, "DETERMINE RELATED DIAGNOSTIC TESTS," in which diagnostic tests, or procedures, that are related to the symptom and subject/unit type can be identified from a pool of diagnostic tests. The diagnostic tests can be, for example, authored by an expert diagnostic technician, or converted from an existing fault tree or a diagnostic FMEA. Each of the diagnostic test procedures can be associated with a specific failure mode of a subject/unit component.

Figure 6:
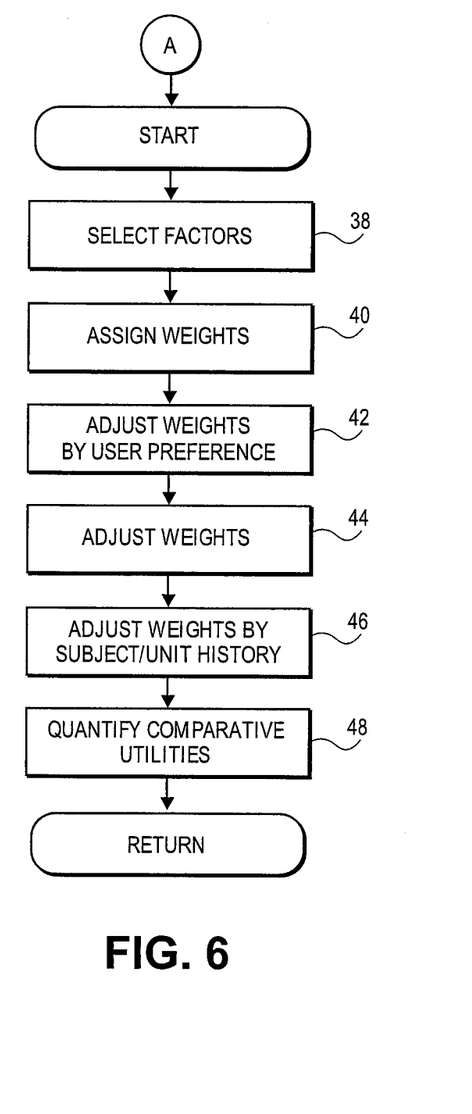
FIG. 6 is a flow chart illustrating steps that may be followed to perform a failure mode analysis that is compatible with the method of FIG. 5.

At this point, in step 36, "PERFORM FAILURE MODE ANALYSIS," a comparative utility of each of the individual diagnostic test procedures can be quantified. FIG. 6 illustrates a method or process for performing a failure mode analysis. In step 38, "SELECT FACTORS," one or more factors that can affect the resolution of a failure mode can be selected for use in the analysis, as described above. Next, in step 40, "ASSIGN WEIGHTS," a weight, or weighting, can be assigned to each of the selected factors in accordance with a priority or preference representing the relative importance of each of the factors with regard to remaining factors.

Control then passes to step 42, "ADJUST WEIGHTS BY USER PREFERENCE," in which each of the weights can be adjusted to reflect a user preference setting, as described above. Next, in step 44, "ADJUST WEIGHTS," each of the weights can be adjusted to reflect the information, such as probability or risk factors from medical manuals, medical databases, service manuals, the FMEA, and the like as described above. In turn, in step 46, "ADJUST WEIGHTS BY SUBJECT/UNIT HISTORY," each of the weights can be adjusted in accordance with the subject/unit history, such as a recommended maintenance procedure that is coming due and has not been performed on the subject/unit, as described above.

Subsequently, in step 48, "QUANTIFY COMPARATIVE UTILITIES," the weighted factors can be used in an algorithm to determine a numerical comparative utility for each of the diagnostic test procedures. For example, the comparative utility can reflect the likelihood that the test procedure will result in resolution of the problem taking into account the time and cost required to perform the diagnostic procedure.

Returning to FIG. 5, in step 50, "ORDER DIAGNOSTIC TESTS," the diagnostic test procedures can be placed in an order that optimizes the overall utility of the diagnostic test sequence. That is, the diagnostic test procedures can be placed in a sequence that optimizes selected factors in accordance with user preferences and the subject/unit history, or other desired factors, as described above.

At this point, in step 52, "SELECT DIAGNOSTIC TESTS FOR DISPLAY," a subset of the diagnostic tests can optionally be selected for display on a display device. Thus, the optimized sequence of diagnostic test procedures can be presented to a medical professional or technician to aide the medical professional or technician in diagnosing a failure mode associated with a subject/unit system.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computer-implemented method of optimizing a diagnostic test sequence to diagnose a medical condition of a subject, comprising:
    determining a group of diagnostic tests related to a symptom of the subject from a pool of diagnostic tests;
    conducting a probabilistic medical condition analysis determining an efficacy of each of the diagnostic tests based on historical outcomes of actual diagnostic testing;
    analyzing a comparative utility of each diagnostic tests based on a plurality of factors that can affect a problem resolution;
    assigning a weight to each factor involved in the probabilistic medical condition analysis;
    ordering the diagnostic tests based upon at least one of the following: a probability of the diagnostic test identifying a cause of the medical condition in a minimum amount of time; a probability of the diagnostic test identifying the cause of the medical condition at a minimum cost; and a relative weighting of minimizing time versus minimizing cost; and
    selecting a first diagnostic test from the group of diagnostic tests based at least in part on the probabilistic medical condition analysis and the weighted factors involved therein.

2. The computer-implemented method according to claim 1 further comprising performing the probabilistic medical condition analysis to quantify the comparative utility of an individual diagnostic test of the group of diagnostic tests.

3. The computer-implemented method according to claim 1, wherein the probabilistic medical condition analysis is based at least on one factor selected from the following: an estimated time required to perform the first diagnostic test, a difficulty of performing the first diagnostic test, an estimated cost to perform the first diagnostic test, and availability of health insurance to pay for the first diagnostic test.

4. The computer-implemented method according to claim 1, wherein the probabilistic medical condition analysis is based on one factor selected from the following: an availability of a medical device to perform the first diagnostic test, an estimated cost of performing the first diagnostic test, an estimated cost per time unit of labor, an empirical data regarding a probability that the medical condition exists given the existence of the symptom, an estimate of the probability that the medical condition exists given the existence of the symptom, a frequency of the medical condition, a medical history of the subject, other pre-existing conditions of the subject, and family medical history of the subject.

5. The computer-implemented method according to claim 1, wherein the weight assigned is based at least in part on a medical professional's preference setting.

6. The computer-implemented method according to claim 1, wherein the probabilistic medical condition analysis is based at least in part on a medical diagnostic test manual.

7. The computer-implemented method according to claim 1 further comprising receiving a medical history of the subject, and wherein the step of selecting the first diagnostic test is further based at least in part on the medical history.

8. The computer-implemented method according to claim 7, wherein the medical history comprises at least one component selected from the following: a pre-existing condition, an age of the subject, a gender of the subject, environmental exposures of the subject, and family medical history of subject.

9. The computer-implemented method according to claim 1, wherein the first diagnostic test has a highest probability of identifying a cause of the symptom in a least amount of time among the group of diagnostic tests based at least in part on the probabilistic medical condition analysis.

10. The computer-implemented method according to claim 1, wherein the first diagnostic test has a highest probability of identifying a cause of the symptom with a lowest cost among the group of diagnostic tests based at least in part on the medical condition analysis.

11. The computer-implemented method according to claim 1, further comprising:
  selecting a plurality of additional diagnostic tests from the group of diagnostic tests based at least in part on the medical condition analysis; and
  ordering the plurality of additional diagnostic tests based at least in part on the probabilistic medical condition analysis.

12. The computer-implemented method according to claim 11, wherein the selecting and ordering of the plurality of additional tests are further based on a decreasing probability of each of the plurality of additional diagnostic tests identifying a cause of the symptom in a least amount of time based on the probabilistic medical condition analysis.

13. The computer-implemented method according to claim 11, wherein the selecting and ordering of the plurality of additional diagnostic tests are further based on a decreasing probability of each of the plurality of additional diagnostic tests identifying a cause of the symptom with a lowest cost based on the probabilistic medical condition analysis.

14. A diagnostic tool for optimizing a diagnostic test sequence to diagnose a medical condition of a subject, comprising:

a diagnostic test selector configured to determine a group of diagnostic tests related to a symptom of the subject from a pool of diagnostic tests;
  a medical condition analyzer configured to determine an efficacy of each of the diagnostic tests of the group of diagnostic tests based on historical outcomes of actual diagnostic testing via a probabilistic medical condition analysis;
  an analyzer configured to analyze a comparative utility of each diagnostic tests of the group of diagnostic tests based on a plurality of factors that can affect a problem resolution;
  a weighter configured to assign a weight to each factor involved in the probabilistic medical condition analysis;
  an orderer configured to order the group of diagnostic tests based upon at least one of the following: a probability of the diagnostic test identifying a cause of the medical condition in a minimum amount of time; a probability of the diagnostic test identifying the cause of the medical condition at a minimum cost; and a relative weighting of minimizing time versus minimizing cost; and
  a sequence optimizer configured to select a first diagnostic test from the group of diagnostic tests based at least in part on a probabilistic medical condition analysis and the weighted factors involved therein.

15. The diagnostic tool according to claim 14, wherein the medical condition analyzer is configured to quantify a comparative utility of an individual diagnostic test of the group of diagnostic tests.

16. The diagnostic tool according to claim 15, wherein the medical condition analyzer is further configured to base the comparative utility on one factor selected from the following: an estimated time required to perform the first diagnostic test, a difficulty of performing the first diagnostic test, an estimated cost to perform the first diagnostic test, and availability of health insurance to pay for the first diagnostic test.

17. The diagnostic tool according to claim 14, wherein the medical condition analyzer is further configured to base a comparative utility on one factor selected from the following: an availability of a medical device to perform the first diagnostic test, an estimated cost of performing the first diagnostic test, an estimated cost per time unit of labor, an empirical data regarding a probability that the medical condition exists given the existence of the symptom, an estimate of the probability that the medical condition exists given the existence of the symptom, a frequency of the medical condition, a medical history of the subject, other pre-existing conditions of the subject, and family medical history of the subject.

18. The diagnostic tool according to claim 15, wherein the weighter is configured to assign the weight to each of the factors selected from the following: an estimated time required to perform the first diagnostic test, a difficulty of performing the first diagnostic test, an estimated cost to perform the first diagnostic test, an empirical data regarding a probability that the medical condition exists given the existence of the symptom, an estimate of the probability that the medical condition exists given the existence of the symptom, a frequency of the medical condition, an age of the subject, a general health of the subject.

19. The diagnostic tool according to claim 14, wherein the weighter is further configured to base the weight on a user preference setting.

20. The diagnostic tool according to claim 14, further comprising a medical history receiver configured to receive a medical history of the subject, and wherein the medical condition analyzer is further configured to base a comparative utility at least in part on the medical history.

21. The diagnostic tool according to claim 14, wherein the sequence optimizer is further configured to order a plurality of additional diagnostic tests from the group of diagnostic tests based at least in part on the probabilistic medical condition analysis.

22. A diagnostic tool for optimizing a diagnostic test sequence to diagnose a medical condition of a subject, comprising:
a diagnostic test selector configured to determine a group of diagnostic tests related to a symptom of the subject from a pool of diagnostic tests;
a sequence optimizer configured to select a first diagnostic test from the group based at least in part on a probabilistic medical condition analysis, the probabilistic medical condition analysis being based on historical outcomes of actual diagnostic testing;
a medical condition analyzer configured to quantify a comparative utility of an individual diagnostic test of the group of diagnostic tests based on a plurality of factors that can affect a problem resolution;
a factor weighter configured to assign a weight to each of a plurality of probabilistic medical condition analysis factors; and
a medical history receiver configured to receive a medical history of the subject, wherein the medical condition analyzer is further configured to base the comparative utility at least in part on the medical history.

23. A computer-implemented method of optimizing a diagnostic test sequence to diagnose a medical condition of a subject, comprising:
determining a group of diagnostic tests related to a symptom of the subject from a pool of diagnostic tests; and
optimizing an order of the group of diagnostic tests, the optimization comprising:
conducting a probabilistic medical condition analysis to determine an efficacy of each of the diagnostic tests of the group based on historical outcomes of actual diagnostic testing;
analyzing a comparative utility of each diagnostic tests of the group of diagnostic tests based on a plurality of factors that can affect a problem resolution;
assigning a weight to each factor involved in the probabilistic medical condition analysis;
selecting a first diagnostic test from the group of diagnostic tests; and
iteratively optimizing the order of the group of diagnostic tests in response to prompting by an intermediate diagnostic test information being received.

24. The method according to claim 23, wherein the probabilistic medical condition analysis is based on one factor selected from the following: an estimated time required to perform the first diagnostic test, a difficulty of performing the first diagnostic test, an estimated cost to perform the first diagnostic test, and availability of health insurance to pay for the first diagnostic test.

25. The method according to claim 23, wherein the probabilistic medical condition analysis is based on one factor selected from the following: an availability of a medical device to perform the first diagnostic test, an estimated cost of performing the first diagnostic test, an estimated cost per time unit of labor, an empirical data regarding a probability that the medical condition exists given the existence of the symptom, an estimate of the probability that the medical condition exists given the existence of the symptom, a frequency of the medical condition of the subject, a medical history of the subject, other pre-existing conditions of the subject, and family medical history of the subject.

26. The method according to claim 23, wherein the factor is selected from one of the following: an estimated time required to perform the first diagnostic test, a difficulty of performing the first diagnostic test, a frequency of the medical condition, an age of the subject, and a general health of the subject.

27. The method according to claim 23, wherein the weight is based on a user preference setting.

28. The method according to claim 23 further comprising receiving a medical history of the subject, wherein the step of selecting the first diagnostic test is further based at least in part on the medical history.

29. The method according to claim 23, wherein the first diagnostic test has a highest probability of identifying a cause of the symptom in a least amount of time among the group based at least in part on the probabilistic medical condition analysis.

30. The method according to claim 23, wherein the first diagnostic test has a highest probability of identifying a cause of the symptom with a lowest cost among the group based at least in part on the probabilistic medical condition analysis.

* * * * *